United States Patent [19]

Korsgaard et al.

[11] Patent Number: 5,919,812
[45] Date of Patent: Jul. 6, 1999

[54] USE OF 3,4-DIPHENYL CHROMANS FOR THE MANUFACTURE OF A PHARMACEUTICAL COMPOSITION FOR THE TREATMENT OR PROPHYLAXIS OF IDIOPATHIC OR PHYSIOLOGIC GYNAECOMASTIA

[75] Inventors: Niels Korsgaard, Værløse; Michael Shalmi, København V; Birgitte Hjort Guldhammer, Hillerød, all of Denmark

[73] Assignee: Novo Nordisk A/S, Bagsvaerd, Denmark

[21] Appl. No.: 08/811,154

[22] Filed: Mar. 4, 1997

Related U.S. Application Data

[63] Continuation of application No. 08/587,869, Jan. 11, 1996, abandoned.

[30] Foreign Application Priority Data

Jan. 13, 1995 [DK] Denmark .................................. 0042/95
Jun. 30, 1995 [DK] Denmark .................................. 0773/95

[51] Int. Cl.$^6$ .................................................. A61K 31/40
[52] U.S. Cl. .......................... 514/422; 514/428; 514/456; 514/874
[58] Field of Search ...................... 514/422, 428, 514/456, 874

[56] References Cited

U.S. PATENT DOCUMENTS

| | | | |
|---|---|---|---|
| 3,822,287 | 7/1974 | Bolger | 260/326.5 D |
| 4,447,622 | 5/1984 | Salman et al. | 548/525 |
| 4,895,715 | 1/1990 | Neri et al. | |
| 5,280,040 | 1/1994 | Labroo et al. | 514/422 |
| 5,364,847 | 11/1994 | Labrie et al. | 514/182 |

OTHER PUBLICATIONS

Srivasta et al., "Mode of Action Of Centchroman At Vaginal And Ovarian Level In Immature Rats", Ind. J. Physiol. Pharmac, Jan.–Mar., 1980, vol. 24, pp. 44–48.

Black et al., "Raloxifene (LY139481 HCI) Prevents Bone Loss and Reduces Serum Cholesterol Without Causing Uterine Hypertrophy In Ovariectomized Rats", J. Clin. Invest., vol. 93, Jan. 1994, pp. 63–69.

Singh, MM, et al., Acta Endocrinologica, vol. 126, pp. 444–450, (1992).

*Primary Examiner*—James H. Reamer
*Attorney, Agent, or Firm*—Steve T. Zelson, Esq.; Cheryl H. Agris, Esq

[57] ABSTRACT

The present invention provides novel uses of compounds of general formula I

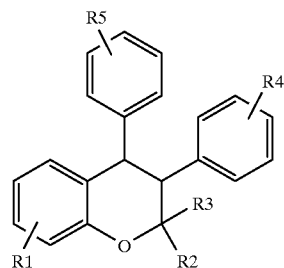

wherein R1, R4 and R5 are individually hydrogen, hydroxy, halogen, trifluoromethyl, lower alkyl, lower alkoxy or (tertiary amino)(lower alkoxy); and R2 and R3 are individually hydrogen or lower alkyl, or as a pharmaceutically acceptable salt thereof in combination with a pharmaceutically acceptable carrier for the manufacture of a pharmaceutical composition for the treatment or prophylaxis of idiopathic or physiologic gynaecomastia.

16 Claims, No Drawings

USE OF 3,4-DIPHENYL CHROMANS FOR THE MANUFACTURE OF A PHARMACEUTICAL COMPOSITION FOR THE TREATMENT OR PROPHYLAXIS OF IDIOPATHIC OR PHYSIOLOGIC GYNAECOMASTIA

This application is a continuation of application Ser. No. 08/587,869 filed Jan. 11, 1996, abandoned which claims priority of Danish applications Serial No. 0042/95 and 0773/95 filed on Jan. 13, 1995 and Jun. 30, 1995, the contents of which are fully incorporated herein by reference.

FIELD OF THIS INVENTION

The present invention relates to the use of compounds of the general formula I for the treatment of patients suffering from idiopathic or physiologic gynaecomastia and prophylaxis hereof. The present invention also embraces pharmaceutical compositions comprising these compounds and methods of using the compounds and their pharmaceutical compositions.

BACKGROUND OF THIS INVENTION

Gynaecomastia is characterised by an increased amount of breast tissue in males. A central issue in the evaluation of breast tissue in adult men is the separation of the normal from the abnormal. In autopsy data (Anderson J A & Groom J B, Acta Pathol Microbiol Immunol Scand 90:191, 1982) the incidence of active gynaecomastia is between 5% and 9%. However, it has been reported (Nutall F Q, J Clin Endocrinol Metab 48:338, 1979; Niewoehner C V & Nutall F Q, Am J Med 77:633, 1984) that approximately 40% of normal men and up to 70% of hospitalized men have palpable breast tissue. The reason for this discrepancy is not clear, but it may suggest that it can be difficult to distinguish true breast tissue from masses of adipose tissue without breast tissue (lipomastia). Alternatively, a true increase in the incidence of gynaecomastia may have taken place, or the autopsy data may underestimate the frequency of palpable breast tissue.

Histologically, early gynaecomastia is characterized by proliferation in the breast of both the fibroblastic stroma and the duct system, which elongates, buds, and duplicates. As gynaecomastia persists, progressive fibrosis and hyalization are associated with regression of epithelial proliferation. Eventually the number of ducts decreases. Resolution occurs by reduction in size and epithelial content with gradual disappearance of the ducts leaving hyaline bands that eventually disappears.

Growth of the breast in men, as in women, is mediated by estrogen and results from disturbances of the normal ratio of active androgen to estrogen in plasma or within the breast itself. Estradiol formation in the normal man occurs principally by the conversion of the circulating androgens to estrogens in peripheral tissues; the normal ratio of production of testosterone to estradiol in adult men is approximately 100:1 (6 mg versus 45 μg), and the normal ratio of the two hormones in plasma is about 300:1. Feminization results when there is a significant decrease in this effective ratio as a result of diminished testosterone production or action, enhanced estrogen production, or both processes occurring simultaneously. The predominant manifestation of feminization in men is enlargement of the breast.

Enlargement of the male breast can occur as a normal physiologic phenomenon at certain stages of life or as the result of different pathologic conditions.

Physiologic gynaecomastia occur in newborns and adolescents as transient enlargements of the breast which normally disappears spontaneously within few weeks to years usually without leaving palpable changes. Gynaecomastia of aging occurs in otherwise healthy men. Forty percent or more of aged men have gynaecomastia. A likely explanation is the increase with age in the conversion of androgens to estrogens in the extraglandular tissues. Abnormal liver function or drug therapy may be contributing causes to gynaecomastia in such men.

Pathologic gynaecomastia can result from one of three basic mechanisms: deficiency in testosterone production or action (with or without a secondary increase in estrogen production), increase in estrogen production, or drugs.

When the primary cause of the overestrogenization can be identified and corrected, the breast enlargement usually subsides promptly and eventually disappears. However, in a number of cases no cause can be found and the gynaecomastia is called idiopathic or physiologic. These cases can in some persons at certain stages of life cause tremendous psychological disturbances. The cause in these cases is always an increased ratio of oestrogen/testosterone. There can be an increased risk of developing breast cancer under these circumstances. Surgery is undesirable in these otherwise healthy men. The most rational way to treat gynaecomastia would be to inhibit the underlying excess stimulation of breast tissue by endogenous oestrogen and to induce atrophy of the breast tissue.

Centchroman is a non-steroidal compound known to have antiestrogenic activity. It is in use in India as an oral contraceptive (see, for example, Salman et al., U.S. Pat. No. 4,447,622; Singh et al., Acta Endocrinal (Copenh) 126 (1992), 444–450; Grubb, Curr Opin Obstet Gynecol 3 (1991), 491–495; Sankaran et al., Contraception 9 (1974), 279–289; Indian Patent Specification No. 129187). Centchroman has also been investigated as an anti-cancer agent for treatment of advanced breast cancer (Misra et al., Int J Cancer 43 (1989), 781–783. Recently, centchroman as a racemate has been found potent as a cholesterol lowering pharmaceutical expressed by a significant decrease of the serum concentrations (S. D. Bain et al., J Min Bon Res 9 (1994), S 394).

U.S. Pat. No. 5,280,040 describes methods and pharmaceutical compositions for reducing bone loss using 3,4-diarylchromans and their pharmaceutically acceptable salts.

There remains today a need in the art for compositions and methods that are useful in the treatment or prophylaxis of idiopathic or physiologic gynaecomastia.

One object of the present invention is to provide compounds which can effectively be used in the treatment or prophylaxis of idiopathic or physiologic gynaecomastia.

BRIEF DESCRIPTION OF THIS INVENTION

It has, surprisingly, been found that compounds of the general formula I as stated in claim 1 can be used in the treatment or prophylaxis of idiopathic or physiologic gynaecomastia.

DETAILED DESCRIPTION OF THIS INVENTION

The present invention is based in part on the discovery that a representative 3,4-diarylchroman, centchroman (3,4-trans-2,2-dimethyl-3-phenyl-4-[p-(beta-pyrrolidinoethoxy)phenyl]-7-methoxychroman) is effective against idiopathic or physiologic gynaecomastia, inter alia in rats. These animal models are generally recognized models of idiopathic or physiologic gynaecomastia. These data thus indicate that the 3,4-diarylchromans are useful as therapeutic or preventive agents against idiopathic or physiologic gynaecomastia in mammals, including primates such as humans.

Within the present invention, compounds of formula I as stated in claim 1 are used for idiopathic or physiologic gynaecomastia in a patient. Within formula I, R1, R4 and R5 are individually hydrogen, halogen, trifluoromethyl, lower alkyl, lower alkoxy or (tertiary amino)(lower alkoxy); and R2 and R3 are individually hydrogen or a lower alkyl. As used herein, the term "lower alkyl" includes straight and branched chain alkyl radicals containing from 1 to 6 carbon atoms, such as methyl, ethyl, n-propyl, isopropyl, n-butyl, tert-butyl, n-amyl, sec-amyl, n-hexyl, 2-ethylbutyl, 2,3-dimethylbutyl and the like. The term "lower alkoxy" includes straight and branched chain alkoxy radicals containing from 1 to 6 carbon atoms, such as methoxy, ethoxy, n-propoxy, isopropoxy, n-butoxy, tert-butoxy, n-amyloxy, sec-amyloxy, n-hexyloxy, 2-ethylbutoxy, 2,3-dimethylbutoxy and the like. "Halogen" includes chloro, fluoro, bromo and iodo. The tertiary amino radical may be a dialkylamine such as a dimethyl, diethyl, dipropyl, dibutyl or a polymethyleneimine, e.g. piperidine, pyrrolidine, N-methylpiperazine or morpholine. Preferred compounds include those in which R1 is lower alkoxy; R2 and R3 are lower alkyl, especially methyl; R4 is hydrogen; and R5 is (tertiary amino)(lower alkoxy) of the polymethyleneimine type. Within particularly preferred embodiments, R1 is in the 7-position and is lower alkoxy, particularly methoxy; each of R2 and R3 is methyl, R4 is hydrogen and R5 is in the 4-position and is a (tertiary amino)(lower alkoxy) radical such as pyrrolidinoethoxy. To be included by this invention are all pharmaceutically acceptable salts of the mentioned compounds of formula I.

It is preferred to use the compounds of formula I in the transconfiguration. These compounds may be used as racemic mixtures, or the isolated d- or l-enantiomers may be used. The trans-l-enantiomers are more preferred.

A particularly preferred compound for use within the present invention is centchroman having the formula IV as stated in the claims below.

Although only one enantiomer is shown, it will be understood that the formula IV is used herein to designate the transconfiguration of the 3- and 4-phenyl groups and that both the d- and l-enantiomers, as well as the racemic mixture, are included.

3,4-diarylchromans are prepared according to known methods, such as those disclosed in U.S. Pat. No. 3,340,276 to Carney et al., U.S. Pat. No. 3,822,287 to Bolger, and Ray et al., *J Med Chem* 19 (1976), 276–279, the contents of which are incorporated herein by reference. Conversion of the cis isomer to the trans configuration by means of an organometallic base-catalyzed rearrangement is disclosed in U.S. Pat. No. 3,822,287. The optically active d- and l-enantiomers may be prepared as disclosed by Salman et al. in U.S. Pat. No. 4,447,622 (incorporated herein by reference) by forming an optically active acid salt which is subjected to alkaline hydrolysis to produce the desired enantiomer.

Within the present invention, 3,4-diarylchromans may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

3,4-diarylchromans and their salts are useful within human and veterinary medicine, for example, in the treatment of patients suffering from idiopathic or physiologic gynaecomastia. For use within the present invention, 3,4-diarylchromans and their pharmaceutically acceptable salts are formulated with a pharmaceutically acceptable carrier to provide a medicament for parenteral, oral, nasal, rectal, subdermal or intradermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release, dermal implants, tablets, etc. One skilled in this art may formulate the compounds in an appropriate manner, and in accordance with accepted practices, such as those disclosed in *Remington's Pharmaceutical Sciences*, Gennaro, ed., Mack Publishing Co., Easton, Pa., 1990.

Oral administration is preferred. Thus, the active compound is prepared in a form suitable for oral administration, such as a tablet or capsule. Typically, a pharmaceutically acceptable salt of the compound is combined with a carrier and moulded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, colouring additives, etc.

Pharmaceutical compositions are administered one or more times per day or week. An effective amount of such a pharmaceutical composition is the amount that provides a clinically significant effect against idiopathic or physiologic gynaecomastia. Such amounts will depend, in part, on the particular condition to be treated, age, weight, and general health of the patient, and other factors evident to those skilled in the art.

The pharmaceutical compositions may be administered in unit dosage form one or more times per day or week. In the alternative, they may be provided as controlled release formulations suitable for dermal implantation. Implants are formulated to provide release of active compound over the desired period of time, which can be up to several years. Controlled-release formulations are disclosed by, for example, Sanders et al., *J Pharm Sci* 73 (1964), 1294–1297, 1984; U.S. Pat. No. 4,489,056; and U.S. Pat. No. 4,210,644, which are incorporated herein by reference.

The following examples are offered by way of illustration, not limitation.

Examples of preferred compounds are centchroman as a racemic mixture and as l-centchroman and d-centchroman. Furthermore, 3,4-trans-2,2-dimethyl-3-phenyl-4-[4-(2-(pyrrolidin-1-yl)ethoxy)phenyl]-7-hydroxychroman is a preferred compound.

A more preferred compound is trans-l-centchroman (l-3,4-trans-2,2-dimethyl-3-phenyl-4-[p-(beta-pyrrolidinoethoxy)phenyl]-7-methoxychroman).

Examples of pharmaceutically acceptable acid addition salts are salts with non-toxic acids, either inorganic acids such as hydrochloric acid, sulphuric acid and phosphoric acid, or organic acids such as formic acid, fumaric acid, acetic acid, propionic acid, succinic acid, gluconic acid, lactic acid, citric acid, ascorbic acid, benzoic acid, embonic acid, methanesulphonic acid and malonic acid.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

Test 1

The competitive antiestrogenic action of centchroman has been demonstrated in uterine tissue from normal sexually mature Sprague-Dawley rats.

Twenty Sprague-Dawley sexually mature female rats (200–225 g) were obtained from Mollegaards breeding center, LI Skensved, Denmark. The rats were housed in metal hanging cages in groups of two and had ad libitum access to food and water for one week. Room temperature was maintained at 20°±1.5° with a minimum relative humidity of 40%. The photoperiod in the room was 12 hours light and 12 hours dark.

After the one week of acclimation period the rats were at random divided into five treatment groups of each 4 rats and daily oral treatment with the test compound was initiated. The test compound was given in five doses (0 mg/kg/day, 5 mg/kg/day, 10 mg/kg/day, 25 mg/kg/day or 75 mg/kg/day) for fourteen days. Following the dosing period the animals were weighed and sacrificed by asphyxiation with $CO_2$, the uterus was removed through a midline incision, and a wet uterine weight was determined after gently blotting on a towel.

Data shown in table I below shows comparative results among the treated rats. Treatment with centchroman in sexually mature rats with intact ovaries induce a significant hypoplasia of the uteri.

TABLE I

| Group | Body weight (g) | Uterus weight (g) | Uterus/body (mg/g) |
|---|---|---|---|
| 0 mg/kg/day | 182 | 0.49 | 2.71 |
| 5 mg/kg/day | 159 | 0.18 | 1.15 |
| 10 mg/kg/day | 165 | 0.21 | 1.25 |
| 25 mg/kg/day | 153 | 0.20 | 1.30 |
| 75 mg/kg/day | 135 | 0.18 | 1.32 |

From this observation it can be concluded that centchroman acts as an antagonist to the normal stimulating effect of oestrogen on the uterus. This was supported by the subsequent microscopy, which revealed an atrophic endometrium in these rats.

Test 2

Between 3 and 25 men having gynaecomastia are administered a compound of the present invention. The amount of compound administered is from 0.1 to 1000 mg/day, and the period of administration is 3 months.

The men are observed during the period of administration, and up to 3 months after discontinuance of administration, for effects on the gynaecomastia.

Test 3

The same procedure as is used in Test 1, except for the period of adminstration is 6 months.

Test 4

The same procedure as is used in Test 1, except for the period of adminstration is 1 year.

Test 5

Prolonged estrogen stimulation is used to induce gynaecomastia in sexually mature male rats. Animals are dosed with estradiol 3–5 times per week by injection for 2–4 months until gynaecomastia arise. Treatment consisting of a compound of the invention or vehicle is administered daily for 3–20 weeks and then animals are sacrificed and the mammary glands harvested and analyzed for regression of gynaecomastia.

Test 6

Tissue from human mammary glands are harvested and maintained, in vitro, as primary non-transforming cultures. Surgical specimens are pushed through a sterile mesh or sieve, or alternatively teased apart from surrounding tissue to produce a single cell suspension. Cells are maintained in media containing 10% serum and antibiotic. Rates of growth in the presence or absence of estrogen are determined. Cells are assayed for their ability to respond to growth factors and growth hormone. Levels of steroid hormones receptors are assessed weekly to determine whether important cell characteristics are maintained in vitro. Tissue from 5–25 patients are utilized.

We claim:

1. A method for treatment or prevention of idiopathic or physiologic gynaecomastia comprising administering to a patient in need of such treatment a compound of formula I

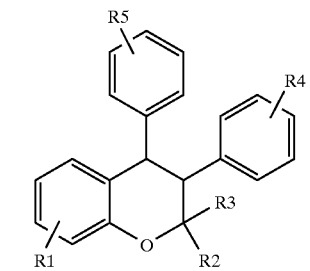

(I)

wherein R1, R4, and R5 are individually hydrogen, hydroxy, halogen, trifluoromethyl, lower alkyl, lower alkoxy or (tertiary amino)(lower alkoxy); and R2 and R3 are individually hydrogen or lower alkyl, or a pharmaceutically acceptable salt thereof in an amount sufficient to treat or prevent idiopathic or physiologic gynaecomastia.

2. The method according to claim 1 in which R1 is lower alkoxy, R2 and R3 are lower alkyl, R4 is hydrogen and R5 is tertiary amino lower alkoxy.

3. The method according to claim 1 wherein R1 is methoxy.

4. The method according to claim 1 wherein R2 is methyl.

5. The method according to claim 1 wherein R3 is methyl.

6. The method according to claim 1 wherein R4 is hydrogen.

7. The method according to claim 1 wherein R5 has the formula II:

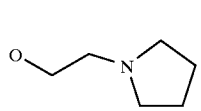
(II)

8. The method according to claim 1 wherein said compound is an isolated d- or l-enantiomer.

9. The method according to claim 1 wherein said compound has the formula III:

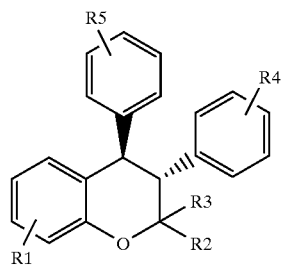
(III)

10. The method according to claim 1 wherein said compound is an isolated l-enantiomer.

11. The method according to claim 1 wherein said compound is centchroman having the formula IV:

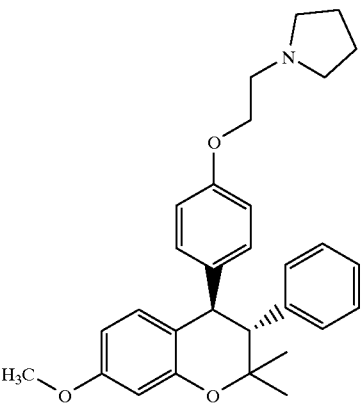
(IV)

12. The method according to claim 11 wherein said compound is an isolated d- or l-enantiomer.

13. The method according to claim 11 wherein said compound is an isolated l-enantiomer.

14. The method according to claim 1 wherein said compound is administered orally.

15. The method according to claim 1 wherein said compound is administered in a range from about 0.001 to 75 mg/kg patient per day.

16. The method according to claim 1 wherein said compound is administered in the form of a dermal implant.

* * * * *